US007022335B2

(12) United States Patent
Hori et al.

(10) Patent No.: US 7,022,335 B2
(45) Date of Patent: Apr. 4, 2006

(54) SUPPOSITORY OF RETAINING IN LOWER REGION OF RECTUM

(75) Inventors: Seiichi Hori, Tokyo (JP); Katsuyoshi Aikawa, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/380,949

(22) PCT Filed: Sep. 12, 2001

(86) PCT No.: PCT/JP01/07893

§ 371 (c)(1),
(2), (4) Date: Mar. 20, 2003

(87) PCT Pub. No.: WO02/24161

PCT Pub. Date: Mar. 28, 2002

(65) Prior Publication Data
US 2003/0185861 A1 Oct. 2, 2003

(30) Foreign Application Priority Data
Sep. 21, 2000 (JP) ............................. 2000-286963

(51) Int. Cl.
*A61F 13/00* (2006.01)
(52) U.S. Cl. .................. 424/433; 424/436; 424/484; 424/486; 424/488; 514/966; 514/967
(58) Field of Classification Search ................ 424/434, 424/436, 433; 514/179, 967, 966
See application file for complete search history.

(56) References Cited
U.S. PATENT DOCUMENTS

| 2,055,063 A | | 9/1936 | Bird | |
|---|---|---|---|---|
| 4,722,941 A | * | 2/1988 | Eckert et al. | 514/784 |
| 4,837,214 A | * | 6/1989 | Tanaka et al. | 514/179 |
| 5,489,576 A | * | 2/1996 | Yoshida et al. | |
| 5,635,520 A | * | 6/1997 | Uda | |
| 5,869,521 A | * | 2/1999 | Farrar et al. | |
| 6,210,698 B1 | * | 4/2001 | Yamazaki et al. | |

FOREIGN PATENT DOCUMENTS

| DE | 291 247 A5 | 6/1991 |
|---|---|---|
| EP | 848948 | 6/1998 |
| EP | 1022019 | 7/2000 |
| JP | 4-346916 | 12/1992 |

OTHER PUBLICATIONS

Database WPI, Section Ch, Week 198830, Derwent Publications, Ltd., London, GB; AN 1988-211408, XP002263776 & SU 1 364 339 A, (FATS RES INST), Jan. 7, 1988 (abstract).
Database WPI, Section Ch, Week 200026, Derwent Publications Ltd., London, GB; AN 2000-301421, XP002263777 & RU 2 128 987, (Nizhegorod Chem Pharm Wks Stock Co), Apr. 20, 1999 (abstract).
Database WPI, Section Ch, Week 198148, Derwent Publications Ltd., London, GB; AN 1981-87958D, XP002263778 and JP 56 131514 A, (Nissan Chem Ind Ltd), Oct. 15, 1981 (abstract).
Abdel Hamid A. El-Shamy, et al., "Formulation and Stability of Aminopyrine in Suppositories," Journal of Drug Research, 1973, pp. 231-238, vol. 5, No. 1, Egypt.
G. Regdon, et al., "Acetylsalicylic acid in suppositories. Effects of viscosity increasing additives on physical and chemical stability," Deutsche Apotheker-Zeitung, 1976, pp. 1280-1282, vol. 116, No. 35.

* cited by examiner

*Primary Examiner*—Thurman K. Page
(74) *Attorney, Agent, or Firm*—Sughrue Mion, PLLC

(57) ABSTRACT

A suppository of retaining in a lower region of rectum, which contains a suppository base containing:
(A) a fatty acid triglyceride,
(B) one or more $C_{14-18}$ fatty acid glycerides, and
(C) a base ingredient for retaining the suppository in the lower region of rectum, has quite high safety, does not melt by the body temperature when it is held by the fingers before insertion into the rectum so that it is easy to handle, does not deform by elevation of temperature during storage, and prevents stimulation to the rectum mucosa such as congestive hemorrhage and expansion of the rectum mucosa after the insertion.

10 Claims, No Drawings

SUPPOSITORY OF RETAINING IN LOWER REGION OF RECTUM

TECHNICAL FIELD

The present invention relates to a suppository, and particularly to a suppository of retaining in the lower region of rectum. More particularly, it relates to a suppository of retaining in the lower region of rectum free from the melting at the time of being held by the fingers and from the deformation of the suppository due to elevation of temperature during storage.

BACKGROUND ART

It is known that a composition for administering to the rectum, which is represented by a usual suppository being administered to the annal region of the rectum, moves from the site where it is administered to the upper region of the rectum with the passage of time, because the suppository base melted by the body temperature and liquefied. Also, an inside temperature of the rectum of human beings varies depending upon the individual differences in body temperature. Furthermore, when the body is affected by pyrexia or pathopoiesis of the rectum, the inside temperature of the rectum changes within a wider range than that in a normal physiological condition of the body. Melting and spreading of a suppository at the annal region of the rectum immediately after the administration reduce the amount of the effective ingredients existing around the annal region of the rectum. For this reason, there have been reported a number of suppository compositions for curing hemorrhoids which control the spreading of molten suppository existing around the annal region of the rectum so that the effective ingredients of the suppository act effectively to the affected regions.

Further, in the usual suppositories, the shape of composition changes with time due to elevation of temperature during storage, etc., and the deformation sometimes is so serious as to make the suppository unusable.

The present applicant reported in WO99/17737 a suppository composition containing a $C_{10-12}$ fatty acid glyceride, which can be kept unmolten in spite of the body temperature even when it is held by the fingers before the insertion into the rectum, melts after the insertion into the rectum, but is free from further spreading of the melted suppository to the upper region of the rectum. However, it has been found that this suppository composition gives stimulation such as congestive hemorrhage or expansion of the rectum mucosa when incorporated with lidocaine, lidocaine hydrochloride, dibucaine, dibucaine hydrochloride, procaine, procaine hydrochloride or ethyl aminobenzoate.

DISCLOSURE OF THE INVENTION

It is an object of the present invention to provide high-safety suppository of retaining in the lower region of the rectum, which is easy to handle, kept unmolten in spite of the body temperature when held by the fingers before the insertion into the rectum, free from deformation of the suppository caused by elevation of temperature during storage, free from the stimulation to the rectum mucosa, and is effective for preventing congestive hemorrhage as well as expansion of the mucosa.

The present inventors have conducted various studies on suppositories of retaining in the lower region of rectum. As a result, they have found that a suppository composition comprising a suppository base comprising:

(A) a fatty acid triglyceride,
(B) one or more $C_{14-18}$ fatty acid glucerides, and
(C) a base ingredient for retaining the suppository in a lower region of rectum, has a melting point exceeding 50° C., can be kept unmolten when held by the fingers before insertion into the rectum so that it is easy to handle, and is free from the deformation of the suppository composition caused by elevation of temperature during storage, able to release the drug satisfactorily, prevented from the simulation to the rectum mucosa, and is very high in safety. Based on this finding, the present invention has been accomplished.

When a conventional suppository composition containing a $C_{10-12}$ fatty acid glyceride which is kept unmolten by the body temperature of fingers while held on the fingers and melts just after the insertion into rectum is compounded with lidocaine or lidocaine hydrochloride, the resulting composition gives stimulations to the rectum mucosa to cause congestive hemorrage or expansion of the rectum mucosa. In contrast, the suppository composition of retaining in the lower region of rectum according to the present invention gives no stimulation to the rectum mucosa even when compounded with lidocaine, lidocaine hydrochloride, dibucaine, dibucaine hydrochloride, procaine, procaine hydrochloride or ethyl aminobenzoate.

Further, the suppository of the present invention is essentially free from $C_{10-12}$ fatty acid glycerides. When a $C_{10-12}$ fatty acid glyceride is present as a subsidiary ingredient in the fatty acid triglyceride or the $C_{14-18}$ fatty acid glyceride, the content of the $C_{10-12}$ fatty acid glyceride should preferably be controlled so that it does not exceed 5% by weight based on the total weight of the suppository base, and further preferably so that it is less than 1% by weight.

Furthermore, incorporation of powders insoluble in the fatty acid triglyceride into the suppository of retaining in the lower region of rectum improves the state of dispersing of the suppository base, which can eliminate the scattering in quality at the time of filling the suppository into a container or mold, thereby to prepare the desired suppository.

The fatty acid triglyceride includes, for example, cacao butter, lanolin butter, medium chain fatty acid triglycerides and hard fats. The hard fats include, for example, "Witepsol" (manufactured by Huls America Inc.), "Sapposier" (manufactured by Gattefosse Inc.), "Isocacao" (manufactured by Kao Corp.) and "Pharmasol" (manufactured by NOF Corp.).

The $C_{14-18}$ fatty acid glyceride includes myristic acid monoglyceride (glycerine ester of $C_{14}$ fatty acid), palmitic acid monoglyceride (glycerine ester of $C_{16}$ fatty acid), and stearic acid monoglyceride (glycerine ester of $C_{18}$ fatty acid), of which preferred are palmitic acid monoglyceride and stearic acid monoglyceride.

The base ingredient for retaining the suppository composition in the lower region of rectum is a base ingredient for administration to rectum which allows a drug to retain in the lower region in the vicinity of annus of rectum. It includes, for example, acrylic acid polymers, alkali metal salts of polygum, laminar silicic acid salt minerals, starch grafted acylates, polyvinyl alcohols, pectins, celluloses, such as methylcellulose and carboxymethylcellulose, etc., polyvinylpyrrolidone, "Pullulan" and tragacanth gum. Of these, one or more of acrylic acid polymers, alkali metal salts of polygum, laminar silicic acid salt minerals and starch grafted acrylic acid are preferable; and acrylic acid polymers are particularly preferable. Of acrylic acid polymers, carboxyvinyl polymers are most preferable.

The powders insoluble in the fatty acid triglyceride include, for example, anhydrous silicic acid, starches, crystalline celluloses, zinc oxide and alginic acid. Of these, anhydrous silicic acid is preferable.

When the total weight of suppository base is taken as 100% by weight, (A) the amount of the fatty acid trigluceride ranges preferably 50–90% by weight and further preferably 65–85% by weight based on the total weight of the suppository, (B) the amount of the oily base consisting of one or more kinds of $C_{14-18}$ fatty acid ester of glycerine is preferably 5–30% by weight and further preferably 6.5–13% by weight based on the total weight of the suppository, and (C) the amount of the base ingredient for retaining the composition in a lower region of rectum ranges preferably 0.1–20% by weight based on the total weight of the suppository. As ingredient (C), acrylic acid polymers are preferable and carboxyvinyl polymer is more preferable. The amount thereof ranges preferably 0.2–15% by weight and further preferably 1–10% by weight based on the total weight of the suppository.

The amount of lidocaine, lidocaine hydrochloride, dibucaine, dibucaine hydrochloride, procaine, procaine hydrochloride or ethyl aminobenzoate ranges preferably 0.1–20% by weight when the total weight of the suppository is taken as 100% by weight.

The amount of the powder insoluble in the fatty acid triglyceride ranges preferably 0.1–20% by weight and further preferably 0.5–10% by weight, when the total weight of the suppository is taken as 100% by weight.

Various drugs can be formulated with the suppository of retaining in the lower region of rectum according to the present invention. The drugs referred to here are those which can generally be administered to the rectum. They include, for example, angiotenic agents, such as "Tetrahydrozoline" hydrochloride, "Naphazoline" hydrochloride, "Phenylephrine" hydrochloride, ephedrine hydrochloride and "Oxymetazoline" hydrochloride; anti-inflammatory, antipyretic, or analgesic agents, such as acetylsalicylic acid, acetoaminophenone, "Buprenorphine" hydrochloride, "Ibprofen", "Ketoprofen", "Proxicam", morphine hydrochloride, lysozyme chloride and glycylrrhetinic acid; antibiotics such as penicillin antibiotics, cephalosporin antibiotics, "Tetracycline" antibiotics and macrolide antibiotics; antineoplastic agents, such as 5-fluorouracil and "Ftorafur"; antifungal agents, such as "Econazole", "Econazole" nitrate, "Miconazole", "Miconazole" nitrate, "Clotrimazole", "Bifonazole", "Terbinafine" hydrochloride and "Butenafine" hydrochloride; steroid preparations, such as hydrocortisone, hydrocortisone acetate, predonisolone, predonisolone acetate, "Dexamethasone" and "Dexamethasone" acetate; local anesthetics such as tetracaine, mepivacain, chloprocaine, bupivacain, proparacain, phenacaine, cocaine, oxyprocain, propitocaine, orthocaine, oxethazaine, tetracaine hydrochloride, mepivacain hydrochloride, chloprocaine hydrochloride, bupivacain hydrochloride, proparacain hydrochloride, phenacaine hydrochloride, cocaine hydrochloride, oxyprocain hydrochloride, propitocaine hydrochloride, "Meprylcaine" hydrochloride and "Mepivacaine"; astringents such as zinc oxide, tannic acid, albumin tannate and aluminum potassium sulfate; antihistamic agents such as diphenhydramine, diphenhydramine hydrochloride and chlorphenylamine maleate; accelerating agents for curing wound, such as allantoin, aluminum chlorohydroxy allantoinate; antiseptics, such as "Chlorhexidine" hydrochloride, "Cetrimide", "Dequalinium" chloride and benzalkonium chloride; sulfa drugs, such as "Sulfisomidine", "Sulfisomidine sodium", "Homosulfamine", and "Sulfadiazine"; vitamins, such as cod liver oils, ergocalciferol, riboflavin, pyridoxine hydrochloride and tocopherol acetate; refrigerants such as d-camphor, dl-camphor, l-menthol, dl-menthol, mentha oil and eucalyptus oil; antiemetics such as "Donperidone"; accelerating agents of defectation, such as "Bisacodyl"; bronchodialators such as theophylline; and peptides such as insulin, etc.

The suppository of the present invention can be prepared by melt-mixing a fatty acid triglyceride, an oil base consisting of a combination of one or more $C_{14-18}$ fatty acid glycerides and an ingredient for retaining the suppository deposited in the lower region of rectum, and if necessary, powders insoluble in the fatty acid triglycerides, adding thereto drugs and additives, uniformly mixing and stirring the resulting mixture, and filling the mixture in a container, mold or the like, and cooling and solidifying the filling. The method for mixing is not specifically restricted.

INDUSTRIAL APPLICABILITY

The present invention relates to a suppository composition particularly useful for treatment of hemorrhoids. More particularly, the present invention relates to a suppository composition of retaining in a lower region of the rectum into which is compounded a suppository base comprising:

(A) a fatty acid trigluceride,
(B) one or more kinds of $C_{14-18}$ fatty acid glycerides, and
(C) a base ingredient for retaining the composition in a lower region of rectum. The composition of the present invention is used as a high-safety suppository for retaining in the lower regions of rectum, which is kept unmolten by the body temperature of fingers when held by the finger before the insertion to rectum, stable to the elevation of temperature during storage, and free from stimulation to the rectum mucosa even when compounded with lidocaine, lidocaine hydrochloride, dibucaine, dibucaine hydrochloride, procaine, procaine hydrochloride and ethyl aminobenzoate.

EXAMPLES

The present invention will be explained in more detail with reference to the following examples and test examples.

Example 1

| (Recipe) | |
|---|---:|
| Tetrahydrozoline hydrochloride | 1.0 g |
| Lidocaine | 60.0 g |
| Hydrocortisone acetate | 5.0 g |
| Allantoin | 20.0 g |
| Tocopherol acetate | 60.0 g |
| Light anhydrous silicic acid | 20.0 g |
| Carboxyvinyl polymer | 34.0 g |
| Myristic acid monoglyceride | 217.5 g |
| Witepsol H15 | 1232.5 g |

(Preparation Method)

A suppository base (myristic acid moonoglyceride and Witepsol H15) was heated and molten (at 50 to 70° C.). Then other ingredients were successively added to the melted suppository base and dispersed therein while stirring. The resulting mixture was cooled, filled in a suppository container, and further cooled and molded to obtain an intended suppository.

Example 2

(Recipe)

| | |
|---|---|
| Phenylephrine hydrochloride | 4.0 g |
| Lidocaine | 82.5 g |
| Light anhydrous silicic acid | 20.0 g |
| Carboxyvinyl polymer | 34.0 g |
| Myristic acid monoglyceride | 226.4 g |
| Pharmasol B115 | 1283.1 g |

(Preparation Method)

The suppository was prepared by the similar method as in Example 1.

Example 3

(Recipe)

| | |
|---|---|
| Phenylephrine hydrochloride | 1.0 g |
| Menthol | 10.0 g |
| Carboxyvinyl polymer | 20.0 g |
| Myristic acid monoglyceride | 126.0 g |
| Palmitic acid monoglyceride | 32.0 g |
| Witepsol H15 | 1424.0 g |

(Preparation Method)

The suppository was prepared by the similar method as in Example 1.

Example 4

(Recipe)

| | |
|---|---|
| Naphazoline hydrochloride | 1.0 g |
| Lidocaine | 60.0 g |
| Prednisolone acetate | 1.0 g |
| Allantoin | 20.0 g |
| Tocopherol acetate | 60.0 g |
| Carboxyvinyl polymer | 34.0 g |
| Laponite | 70.0 g |
| Stearic acid monoglyceride | 74.0 g |
| Witepsol H15 | 1400.0 g |

(Preparation Method)

The suppository was prepared by the similar method as in Example 1.

Example 5

(Recipe)

| | |
|---|---|
| Phenylephrine hydrochloride | 4.0 g |
| Lidocaine | 82.5 g |
| Zinc oxide | 8.5 g |
| Light anhydrous silicic acid | 20.0 g |
| Carboxyvinyl polymer | 34.0 g |
| Myristic acid monoglyceride | 214.0 g |
| Pharmasol B115 | 1213.0 g |

(Preparation Method)

The suppository was prepared by the similar method as in Example 1.

Example 6

(Recipe)

| | |
|---|---|
| Hydrocortisone acetate | 5.0 g |
| Lidocaine | 60.0 g |
| Carboxyvinyl polymer | 33.0 g |
| Light anhydrous silicic acid | 20.0 g |
| Myristic acid monoglyceride | 229.8 g |
| Witepsol E85 | 260.4 g |
| Witepsol W35 | 1041.8 g |

(Preparation Method)

The suppository was prepared by the similar method as in Example 1.

Example 7

(Recipe)

| | |
|---|---|
| Hydrocortisone acetate | 5.0 g |
| Lidocaine | 60.0 g |
| Carboxyvinyl polymer | 33.0 g |
| Light anhydrous silicic acid | 20.0 g |
| Myristic acid monoglyceride | 229.8 g |
| Witepsol E85 | 260.4 g |
| Witepsol W35 | 1041.8 g |

(Preparation Method)

The suppository was prepared by the similar method as in Example 1.

Example 8

(Recipe)

| | |
|---|---|
| Hydrocortisone acetate | 5.0 g |
| Lidocaine | 60.0 g |
| Carboxyvinyl polymer | 33.0 g |
| Light anhydrous silicic acid | 20.0 g |
| Palmitic acid monoglyceride | 76.6 g |
| Stearic acid monoglyceride | 153.2 g |
| Witepsol E85 | 260.4 g |
| Witepsol W35 | 1041.8 g |

(Preparation Method)

The suppository was prepared by the similar method as in Example 1.

Example 9

(Recipe)

| | |
|---|---|
| Hydrocortisone acetate | 5.0 g |
| Lidocaine | 60.0 g |
| Carboxyvinyl polymer | 33.0 g |
| Light anhydrous silicic acid | 20.0 g |
| Palmitic acid monoglyceride | 153.2 g |
| Stearic acid monoglyceride | 76.6 g |
| Witepsol E85 | 260.4 g |
| Witepsol W35 | 1041.8 g |

(Preparation Method)

The suppository was prepared by the similar method as in Example 1.

Example 10

(Recipe)

| | |
|---|---|
| Hydrocortisone acetate | 5.0 g |
| Lidocaine | 60.0 g |
| Carboxyvinyl polymer | 33.0 g |
| Light anhydrous silicic acid | 20.0 g |
| Palmitic acid monoglyceride | 149.9 g |
| Witepsol E85 | 269.8 g |
| Witepsol W35 | 1079.3 g |

(Preparation Method)

The suppository was prepared by the similar method as in Example 1.

Example 11

(Recipe)

| | |
|---|---|
| Hydrocortisone acetate | 5.0 g |
| Lidocaine | 60.0 g |
| Carboxyvinyl polymer | 66.0 g |
| Light anhydrous silicic acid | 20.0 g |
| Stearic acid monoglyceride | 149.9 g |
| Witepsol E85 | 269.8 g |
| Witepsol W35 | 1079.3 g |

(Preparation Method)

The suppository was prepared by the similar method as in Example 1.

Example 12

(Recipe)

| | |
|---|---|
| Hydrocortisone acetate | 5.0 g |
| Lidocaine | 60.0 g |
| Carboxyvinyl polymer | 66.0 g |

-continued (Recipe)

| | |
|---|---|
| Light anhydrous silicic acid | 20.0 g |
| Palmitic acid monoglyceride | 75.0 g |
| Stearic acid monoglyceride | 75.0 g |
| Witepsol E85 | 269.8 g |
| Witepsol W35 | 1079.3 g |

(Preparation Method)

The suppository was prepared by the similar method as in Example 1.

Example 13

(Recipe)

| | |
|---|---|
| Hydrocortisone acetate | 5.0 g |
| Lidocaine | 60.0 g |
| Carboxyvinyl polymer | 66.0 g |
| Light anhydrous silicic acid | 20.0 g |
| Palmitic acid monoglyceride | 60.0 g |
| Stearic acid monoglyceride | 60.0 g |
| Witepsol E85 | 275.4 g |
| Witepsol W35 | 1103.7 g |

(Preparation Method)

The suppository was prepared by the similar method as in Example 1.

Comparative Example 1

(Recipe)

| | |
|---|---|
| Hydrocortisone acetate | 5.0 g |
| Lidocaine | 60.0 g |
| Carboxyvinyl polymer | 33.0 g |
| Light anhydrous silicic acid | 20.0 g |
| Capric acid monoglyceride | 163.8 g |
| Lauric acid monoglyceride | 491.4 g |
| Witepsol H15 | 982.9 g |

(Preparation Method)

The suppository was prepared by the similar method as in Example 1.

Comparative Example 2

(Recipe)

| | |
|---|---|
| Hydrocortisone acetate | 5.0 g |
| Lidocaine | 60.0 g |
| Carboxyvinyl polymer | 33.0 g |
| Light anhydrous silicic acid | 20.0 g |
| Lauric acid monoglyceride | 245.7 g |
| Witepsol H15 | 1392.4 g |

(Preparation Method)

The suppository was prepared by the similar method as in Example 1.

Comparative Example 3

| (Recipe) | |
|---|---|
| Hydrocortisone acetate | 5.0 g |
| Lidocaine | 60.0 g |
| Carboxyvinyl polymer | 33.0 g |
| Light anhydrous silicic acid | 20.0 g |
| Lauric acid monoglyceride | 306.4 g |
| Witepsol H15 | 1225.6 g |

(Preparation Method)

The suppository was prepared by the similar method as in Example 1.

Comparative Example 4

| (Recipe) | |
|---|---|
| Hydrocortisone acetate | 5.0 g |
| Lidocaine | 60.0 g |
| Carboxyvinyl polymer | 65.0 g |
| Light anhydrous silicic acid | 20.0 g |
| Witepsol E85 | 300.0 g |
| Witepsol H15 | 1200.0 g |

(Preparation Method)

The suppository was prepared by the similar method as in Example 1.

Test Example 1

Test on Stimulation to Rectum Mucosa Test Method

As the test samples, the suppository compositions of rectum-retaining type according to Examples 6–13 of the present invention and the suppository compositions of Comparative Examples 1–3 in which a $C_{10}$ and/or $C_{12}$ fatty acid glyceride was compounded were used. In all the test samples, each suppository weighed about 1.65 g. In the test group, Japanese white strain male rabbits (body weight: 3.0–3.5 Kg) were used. The rabbits were in good systemic condition without having diarrhea after fasted for 48 hours. Two or three rabbits were used for each of the suppository test samples.

Method of administration of the suppository test sample was as follows. Thus, one grain of a suppository test sample was inserted into the rectum of the rabbit fasted for 48 hours beforehand, then the anus of the rabbit was pressed by the finger of an experimenter for several ten seconds for the purpose of preventing escape of the inserted suppository, further the anus was closed and sealed tightly by use of an adhesive (Alon-alpha GEL-10: manufactured by Toagosei Co. Ltd.). The rabbit was allowed to water freely until autopsy.

(Observation of the Stimulation to the Rectum Mucosa:)

5 Hours after the administration of suppository test sample, the rabbits in each of the test groups were subjected to euthanasia by bleeding from the carotid artery under anesthesia with pentobarbital. The intestines involving rectum and colon were enucleated from the anus. The enucleated intestines were incised. The mucosal membranes of intestines were washed with physiological saline. Thereafter, the incised intestines were extended on a flat plate, and the mucosal membranes were macroscopically observed. Congestive hemorrhage and expansions appearing on the rectum mucosa were examined by macroscopical observation, and the results were rated as stimulation scores. The stimulation scores were defined as follows:

| | Score |
|---|---|
| No change: | 0 |
| Little change: | 1 |
| Slight change: | 2 |
| Mediocre change: | 3 |
| Marked change: | 4 |

(Test Results:)

Test results are shown in Table 1.

TABLE 1

| Stimulation scores | | | | | | | | | |
|---|---|---|---|---|---|---|---|---|---|
| | Example 6 | | Example 7 | | Example 8 | | Example 9 | | |
| Score | 2 | 2 | 2 | 2 | 2 | 0 | 0 | 0 | 1 |
| | Example 10 | | Example 11 | | Example 12 | | Example 13 | | |
| Score | 0 | 0 | 0 | 0 | 0 | 0 | 0 | 0 | 0 |
| | Comparative Example 1 | | Comparative Example 2 | | Comparative Example 3 | | | | |
| Score | 2 | 3 | 3 | 4 | 4 | 3 | 4 | 2 | 1 |

The suppositories of Comparative Examples 1–3 gave a mediocre or marked stimulation such as congestive hemorrhage and expansions to the rectum mucosa. The suppositories of Examples 6–13 according to the present invention, however, gave no stimulation or gave only a slight stimulation to the rectum mucosa. Thus it has been proved that the suppositories of the present invention are much higher in safety than the suppositories of comparative examples.

Test Example 2

Measurement of Melting Point of Suppository

Test Method:

As the test samples, the suppositories of Examples of 8–13 according to the present invention and the suppository of Comparative Example 4 as a conventional suppository of retaining in the lower region of rectum were used. The melting points were measured by means of Automatic Dropping Melting Point Measuring Apparatus (FP80 and FP83, manufactured by Mettler Corp.). Each sample was filled into a cup having a diameter of 6.35 mm and the temperature was elevated at a rate of 0.2° C./minute. The dropping softening point (° C.) was taken as the melting point. Results:

The melting points determined are listed in Table 2.

TABLE 2

| | Melting point (° C.) | | |
|---|---|---|---|
| | Example 8 | Example 9 | Example 10 |
| Melting point | 58.3 | 57.0 | 55.0 |
| | Example 11 | Example 12 | Comparative Example 4 |
| Melting point | 56.0 | 54.7 | 38.7 |

Melting points of the suppositories of Examples 8–12 according to the present invention exceeded 50° C. Melting point of the suppository of Comparative Example 4 was lower than 40° C.

The results shown above demonstrate that the suppositories of Examples 8–12 according to the present invention have a melting point much higher than the body temperature of human beings, and therefore these suppositories are entirely free from the risk of melting while being held on figures before insertion into the rectum. In contrast, the suppository of Comparative Example 4 has a risk of melting while it is held between fingers when the body temperature is high due to pyrexia. Further, the suppository of Comparative Example 4 has a risk of deforming its shape due to softening or melting if temperature rises under the condition of storage, while the suppositories of Examples 8–12 according to the present invention are free from deformation due to softening so far as the elevation in temperature does not exceed that under usual conditions of storage. Accordingly, it has been proved that the suppositories of the present invention are excellent in the handling property.

Test Example 3

Measurement of Drug-Releasing Rate

Test Method:

A drug-releasing test was carried out by the use of Elution Tester (manufactured by Toyama Sangyo Co., Ltd.) used according to the second method of Method for Elutioh Test, Japanese Pharmacopoeia (paddle method). As the test solution, 900 ml of phosphate buffer solution (pH 7.2) was used. The speed of rotation of the paddle was 100 rpm. A suppository was packed within an area having a width of 5 cm in a membrane filter (Dialysis Membrane, Size 36; manufactured by Wako Pure Chemical Industries, Ltd.) previously immersed in the buffer solution by the use of two closers. The test was carried out at 37° C., and 1 ml portion was sampled out every one hour. The test was continued till the overall time of test reached 6 hours. The samples taken were quantitatively analyzed by HPLC.

| Conditions of HPLC Quantitative Analysis | |
|---|---|
| Column: | ODS-80 Ts (Tosoh Corp.) |
| Column temperature: | 50° C. |
| Mobile phase: | Methanol:Water:Phosphoric Acid:Sodium Laurate = 60:40:0.1:0.5 |
| Flow rate: | 1 ml/min. |
| Injection amount: | 1 µl |
| Wavelength of detection: | 220 nm |

As the samples, the suppositories of Examples 13–16 of the present invention and the suppository of Comparative Exampel 4 were used.

Lidocaine

Results:

TABLE 3

| | Drug releasing rate (%) | | |
|---|---|---|---|
| | Example 13 | Example 14 | Example 15 |
| Release (%) | 45.1 | 39.0 | 32.1 |
| | Example 16 | Comparative Example 4 | |
| Release (%) | 40.3 | 38.8 | |

The suppositories of Examples 13–16 according to the present invention showed a good lidocaine-releasability comparable to that of the suppository of Comparative Example 4. Accordingly, it has been proved that the suppositories of the present invention have no problem with regard to drug-releasability.

The invention claimed is:

1. A suppository comprising a suppository base and one or more active ingredients selected from the group consisting of lidocaine, lidocaine hydrochloride, dibucaine, dibucaine hydrochloride, procaine, procaine hydrochloride and ethyl aminobenzoate;
   wherein said suppository base comprises:
   (A) a fatty acid triglyceride in an amount of from 50–90% of the total weight of the suppository base,
   (B) one or more $C_{14-18}$ fatty acid glycerides in an amount of from 5–30% of the total weight of the suppository base, wherein said one or more $C_{14-18}$ fatty acid glycerides is selected from the group consisting of myristic acid monoglyceride, palmitic acid monoglyceride and stearic acid monoglyceride, and
   (C) a base ingredient for retaining the suppository in a lower region of a rectum, wherein said base ingredient is present in an amount of from 0.1–20% of the total weight of the suppository base, and said base ingredient is one or more members selected from the group consisting of an acrylic acid polymer, an alkali metal salt of polygum, a laminar silicic acid salt mineral, a starch grafted acylate, a polyvinyl alcohol, a pectin, a cellulose, a polyvinylpyrrolidone, a pullulan, and a tragacanth gum;
   wherein total $C_{10-12}$ fatty acid glyceride in the suppository base does not exceed 5% of the total weight of the suppository base.

2. A suppository according to claim 1, wherein said base ingredient for retaining the suppository in the lower region of the rectum is one or more members selected from the group consisting of an acrylic acid polymer, an alkali metal salt of polygum, a laminar silicic acid salt mineral, and a starch-grafted acrylic acid.

3. A suppository according to claim 1, wherein said base ingredient for retaining the suppository in the lower region of the rectum is one or more members selected from the group consisting of a carboxyvinyl polymer, methyl cellulose, and carboxymethylcellulose.

4. A suppository according to claim 1, wherein said suppository base further comprises a powder insoluble in fatty acid triglyceride.

5. A suppository according to claim 1, wherein said suppository base further comprises anhydrous silicic acid.

6. A suppository according to claim 1, wherein total $C_{10-12}$ fatty acid glyceride in the suppository base is less than 1% of the total weight of the suppository base.

7. The suppository of claim 1, wherein said one or more active ingredients are present in an amount of from 0.1–20% of the total weight of the suppository.

8. The suppository of claim 1, wherein said fatty acid triglyceride is present in an amount of from 65–85% of the total weight of the suppository base.

9. The suppository of claim 8, wherein said one or more $C_{14-18}$ fatty acid glycerides is present in an amount of from 6.5–13% of the total weight of the suppository base.

10. The suppository of claim 9, wherein said base ingredient for retaining the suppository in the lower region of the rectum is present in an amount of from 1–10% of the total weight of the suppository base.

* * * * *